United States Patent
Stoeckel

(10) Patent No.: US 7,688,995 B2
(45) Date of Patent: Mar. 30, 2010

(54) SYSTEM AND METHOD FOR QUALITY ASSURANCE FOR DISTRIBUTED COMPUTER AIDED DIAGNOSIS SOLUTIONS

(75) Inventor: Jonathan Stoeckel, RB Hierden (NL)

(73) Assignee: Siemens Medical Solutions USA, Inc., Malvern, PA (US)

(*) Notice: Subject to any disclaimer, the term of this patent is extended or adjusted under 35 U.S.C. 154(b) by 916 days.

(21) Appl. No.: 11/493,309

(22) Filed: Jul. 26, 2006

(65) Prior Publication Data
US 2007/0036412 A1    Feb. 15, 2007

Related U.S. Application Data

(60) Provisional application No. 60/705,541, filed on Aug. 4, 2005.

(51) Int. Cl.
*G06K 9/00* (2006.01)
(52) U.S. Cl. .................... 382/100; 382/128
(58) Field of Classification Search .......... 382/100, 382/128, 131, 132
See application file for complete search history.

(56) References Cited

U.S. PATENT DOCUMENTS

| | | | |
|---|---|---|---|
| 5,765,176 A | * | 6/1998 | Bloomberg ............. 715/209 |
| 6,463,433 B1 | | 10/2002 | Baclawski |
| 7,313,696 B2 | * | 12/2007 | de Queiroz ............. 713/168 |
| 7,328,455 B2 | * | 2/2008 | Jutzi et al. ............. 726/26 |
| 2002/0060736 A1 | * | 5/2002 | Wakao et al. ............. 348/207 |

FOREIGN PATENT DOCUMENTS

WO    WO 2005/001742 A2    1/2005
WO    WO 2005/017806 A     2/2005

OTHER PUBLICATIONS

Zhou et al., "Authencity and Integrity of Digital Mammography Images", IEEE Transactions on Medical Imaging, IEEE Service Center, Piscataway, NJ, vol. 20, No. 8, Aug. 2001, pp. 784-791.

* cited by examiner

*Primary Examiner*—Tom Y Lu

(57) ABSTRACT

A method for associating a computer aided detection/diagnosis result with an image including the steps of providing one or more digitized images, each image comprising a plurality of intensities corresponding to a domain of points on an N-dimensional grid, performing a computer-aided detection/diagnosis of intensity data of a first image, calculating a hash signature of intensity of a second input image, storing said computer-aided diagnosis results, and storing said hash signature, wherein said hash signature verifies said second image when said second image is displayed with said computer-aided diagnosis result.

24 Claims, 2 Drawing Sheets

SYSTEM AND METHOD FOR QUALITY ASSURANCE FOR DISTRIBUTED COMPUTER AIDED DIAGNOSIS SOLUTIONS

CROSS REFERENCE TO RELATED UNITED STATES APPLICATIONS

This application claims priority from "Automatic system for quality assurance for distributed Computer Aided Diagnosis (CAD) solutions", U.S. Provisional Application No. 60/705,541 of Jonathan Stoeckel, filed Aug. 4, 2005, the contents of which are incorporated herein by reference.

TECHNICAL FIELD

This invention is directed to quality assurance in distributed CADS systems.

DISCUSSION OF THE RELATED ART

Computer aided/assisted image based aided diagnosis/detection solutions are used more and more in clinical practice, a widely used example of which being computer aided detection of lesions in mammography. Other applications are also already on the market, e.g. systems for the detection of lung nodules, and other applications will probably follow.

Such a solution mainly comprises a system for receiving the image(s), which can be 2D, 3D, time series images, multi modality images, etc., as an input, an algorithm to process the images and to outputs the results. Results can be any of the following: 2D or 3D coordinates, textual descriptions, other images etc., or combinations thereof.

Such results are then subsequently visualized by a system to the user when diagnosing the patient. In many cases the system will display the images that had been used as input to the CAD system and display the results superimposed (e.g. when results are coordinates) or next to the original images. Examples of such systems are PACS solutions, or special medical workstations.

In many circumstances the CAD system is not run on the system used for visualization or is not run at the same time the results are viewed by the user. This distributed character means that the visualization system has to obtain the CAD results from somewhere else, such as a database or file system over the internet or an intranet etc. This is currently done by looking up the results by using combinations of one or more of the following (called keys in this context): patient name, birth date, gender, date of examination, exam type, SUID of the volume etc.

However, in practice, between the time the CAD system has run and the results are be displayed any of that information might have changed (e.g. patient name corrected because two patient exams were inverted) causing the keys to no longer point to the same images. This means that the visualization system might display images of one patient or examination while at the same time displaying unrelated CAD results related to another patient or examination.

SUMMARY OF THE INVENTION

Exemplary embodiments of the invention as described herein generally include methods and systems for ensuring that a display system can easily insure that the CAD results being shown correspond to the images being shown or having been selected by the user. This has applications in large multi-vendor environments where there could be discrepancies in the data between the systems used (e.g. for patient scheduling, the radiology information system, the PACS system and the dicom headers) to provide information to the visualization system and the CAD system. A method and system according to an embodiment of the invention ensures that correct results are shown without needing changes to data storage systems already in use.

According to an aspect of the invention, there is provided a method for associating a computer aided detection/diagnosis result with an image including the steps of providing one or more digitized images, each image comprising a plurality of intensities corresponding to a domain of points on an N-dimensional grid, performing a computer-aided detection/diagnosis of intensity data of a first image, calculating a hash signature of intensity of a second input image, storing said computer-aided diagnosis results, and storing said hash signature, wherein said hash signature verifies said second image when said second image is displayed with said computer-aided diagnosis result.

According to a further aspect of the invention, the second image is not used as input to said computer aided diagnosis.

According to a further aspect of the invention, the second image is provided as input for said computer-aided detection/diagnosis.

According to a further aspect of the invention, the method comprises storing a locator for said input image with said computer-aided diagnosis results.

According to a further aspect of the invention, the method comprises storing the input image along with said computer-aided diagnosis results.

According to a further aspect of the invention, calculating a hash signature comprises submitting said input image to a hash function calculator system that calculates said hash signature.

According to a further aspect of the invention, the method comprises submitting identifying information for said input image to said hash function calculator system for calculating said hash signature.

According to a further aspect of the invention, the identifying information includes one or more of an image locator, a patient's name, a patient's birth date, a patient's gender, a date of patent's examination wherein said input image was created, an exam type, and a unique identifier of said input image.

According to a further aspect of the invention, the computer-aided diagnosis results and said hash signature are stored together in a same file.

According to another aspect of the invention, there is provided a program storage device readable by a computer, tangibly embodying a program of instructions executable by the computer to perform the method steps for associating a computer aided detection/diagnosis result with a medical image.

DETAILED DESCRIPTION OF THE PREFERRED EMBODIMENTS

Figure 1:
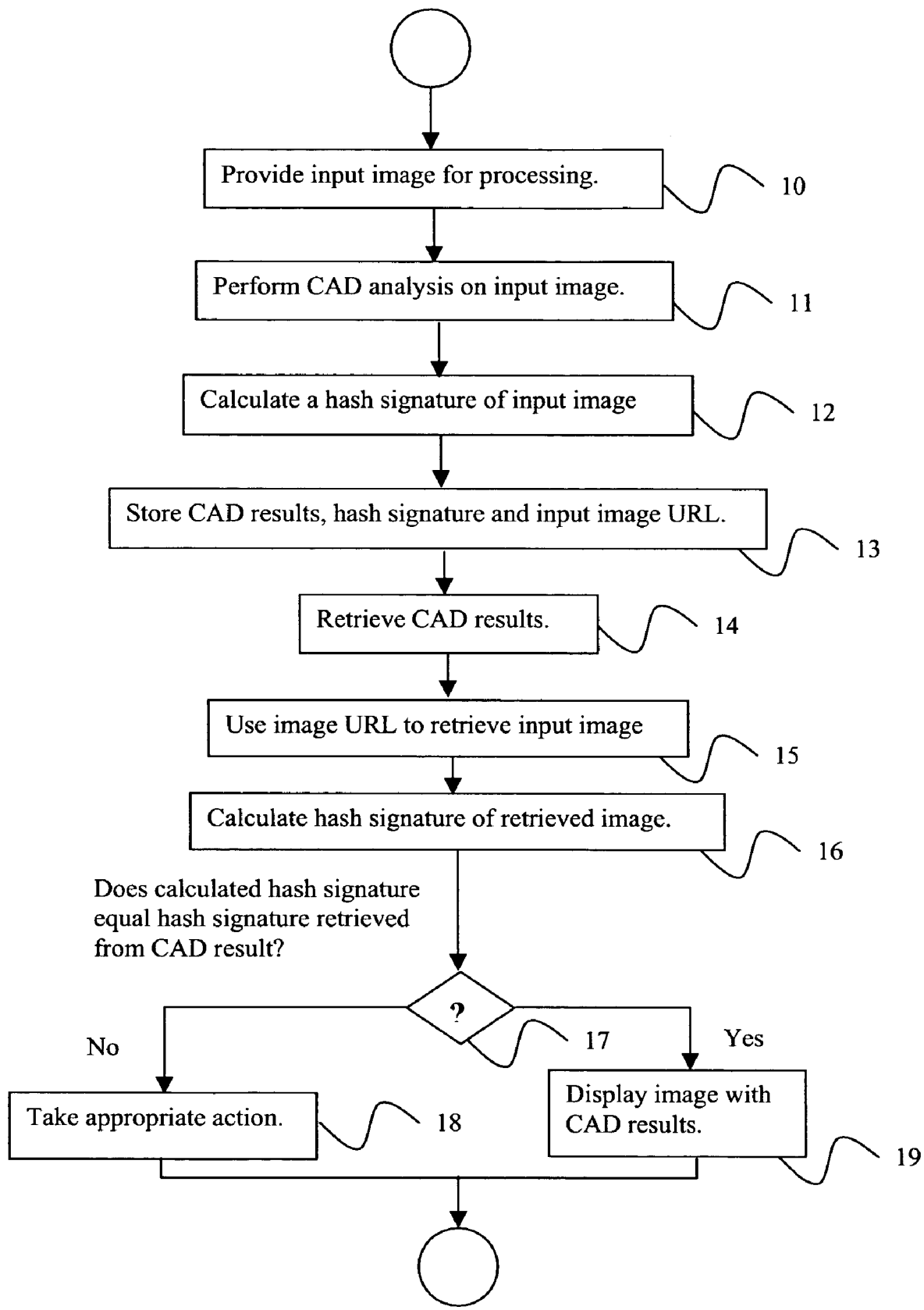
FIG. 1 depicts a flow chart of a quality assurance method according to an embodiment of the invention.

Exemplary embodiments of the invention as described herein generally include systems and methods for ensuring correspondence between CAD results and images. Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

As used herein, the term "image" refers to multi-dimensional data composed of discrete image elements (e.g., pixels for 2-D images and voxels for 3-D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R, the methods of the inventions are not limited to such images, and can be applied to images of any dimension, e.g. a 2-D picture or a 3-D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

A CAD system according to an embodiment of the invention calculates hash(es)/signature(s) on the image(s) themselves that are processed by the CAD system for its analysis. The hash codes should be based on the image itself, so that if, for example, the patient's name is changed (e.g., due to a typo in the original DICOM header, or if two patient names were accidentally swapped and corrected afterwards), the system will still be able to know that CAD was performed for this specific image. These hash codes can be stored together with the CAD results. Such a hash signature can be calculated using one of the many largely and well-described methods available. In addition to including hash signatures, the CAD results also include locators for the input images, such as the file names of the images or their URLs.

A hash function H maps a value from a set with many (or even an infinite number of) members to a value from a set with a fixed number of (fewer) members. Hash functions are not reversible. A exemplary hash function H can be defined as $y=H(x)=\lfloor 10x(\bmod\ 10)\rfloor$, where $x \in R$, $y \in [0 \ldots 9]$, and $\lfloor x \rfloor$ is the floor function.

A hash function can create a small digital "fingerprint" from any kind of data. The function chops and mixes the data to create the fingerprint, often called a hash value. The hash value is commonly represented as a short string of random-looking letters and numbers (data written in hexadecimal notation). A good hash function is one that yields few hash collisions in expected input domains. A hash collision is a situation that occurs when two distinct inputs into a hash function produce identical outputs. Most hash functions have potential collisions, but with good hash functions they occur less often than with bad ones. In certain specialized applications where a relatively small number of possible inputs are all known ahead of time it is possible to construct a perfect hash function which maps all inputs to different outputs. But in a function which can take input of arbitrary length and content and returns a hash of a fixed length here will always be collisions, because any given hash can correspond to an infinite number of possible inputs.

Hash functions can be used to determine if two objects are equal (possibly with a fixed average number of mistakes). Other common uses of hash functions are checksums over a large amount of data and finding an entry in a database by a key value. In hash tables and data processing, collisions inhibit the distinguishing of data, making records more costly to find.

A fundamental property of all hash functions is that if two hashes (according to the same function) are different, then the two inputs are different in some way. This property is a consequence of hash functions being deterministic. On the other hand, a hash function is not injective, i.e. the equality of two hash values strongly suggests, but does not guarantee, the equality of the two inputs. If a hash value is calculated for a piece of data, and then one bit of that data is changed, a hash function with strong mixing property usually produces a completely different hash value.

Typical hash functions have an infinite domain, such as byte strings of arbitrary length, and a finite range, such as bit sequences of some fixed length. In certain cases, hash functions can be designed with a one-to-one mapping between an identically sized domain and range. Hash functions that are one-to-one are also called permutations. Reversibility is achieved by using a series of reversible "mixing" operations on the function input.

Because of the variety of applications for hash functions (details below), they are often tailored to the application. For example, cryptographic hash functions assume the existence of an adversary who can deliberately try to find inputs with the same hash value. A well designed cryptographic hash function is a "one-way" operation: there is no practical way to calculate a particular data input that will result in a desired hash value, so it is also very difficult to forge. Functions intended for cryptographic hashing are commonly used as stock hash functions.

Functions for error detection and correction focus on distinguishing cases in which data has been disturbed by random processes. When hash functions are used for checksums, the relatively small hash value can be used to verify that a data file of any size has not been altered.

Hash tables, a major application for hash functions, enable fast lookup of a data record given its key. For example, keys in an English dictionary would be English words, and their associated records would contain definitions. In this case, the hash function must map alphabetic strings to indexes for the hash table's internal array. The generally impossible/impractical ideal for a hash table's hash function is to map each key to a unique index, a situation referred to as perfect hashing, because this guarantees access to each data record in the first probe into the table.

Hash functions that are truly random with uniform output are good in that, on average, only one or two probes will be needed, depending on the load factor. The load factor is the ratio of the number of records to the number of addresses or indexes within a data structure. Perhaps as important is that excessive collision rates with random hash functions, where a hash collision is a situation that occurs when two distinct inputs into a hash function produce identical outputs, are highly improbable, if not computationally infeasible for an adversary. However, a small, predictable number of collisions is virtually inevitable.

In many cases, a heuristic hash function can yield many fewer collisions than a random hash function. Heuristic functions take advantage of regularities in likely sets of keys. For example, one could design a heuristic hash function such that file names such as FILE0000.CHK, FILE0001.CHK, FILE0002.CHK etc., map to successive indices of the table, meaning that such sequences will not collide. Beating a random hash function on "good" sets of keys usually means performing much worse on "bad" sets of keys, which can arise naturally, not just through attacks. Bad performance of a hash table's hash function means that lookup can degrade to a costly linear search.

Aside from minimizing collisions, the hash function for a hash table should also be fast relative to the cost of retrieving a record in the table, as the goal of minimizing collisions is minimizing the time needed to retrieve a desired record. Consequently, the optimal balance of performance characteristics depends on the application.

Using a hash function to detect errors in transmission is straightforward. The hash function is computed for the data at the sender, and the value of this hash is sent with the data. The hash function is performed again at the receiving end, and if the hash values do not match, an error has occurred at some point during the transmission. This is called a redundancy check. For error correction, a distribution of likely perturbations is assumed at least approximately. Perturbations to a string are then classified into large (improbable) and small (probable) errors. The second criterion is then restated so that if one is given H(x) and x+s, then one can compute x efficiently if s is small. Such hash functions are known as error correction codes.

Thus, after retrieving CAD results from their storage/transfer location, the display/visualization system can use the image file locators included with the results to find the input images, and recalculate these hash signature(s) on the input images. The signatures can be compared with those having been calculated by the CAD system. If the signatures do not match the hash codes stored with the CAD results, the display/visualization system knows it has the wrong results. The system can then take appropriate action, such as warning the user, prompting the user for help, requesting that the CAD system run again, etc.

The display system and the CAD system should be using the same hash function. This could be ensured by designing the display system and CAD system to use the same hash function, or by providing a central service to which both the CAD system and the display system can send the image(s) to obtain a has signature. Note however, that if the display system and CAD system use different hash functions, the hash codes would not match, so that the user of the systems would, in any event, know that something was amiss.

A flow chart of a quality assurance method according to an embodiment of the invention is shown in FIG. 1. Referring now to the figure, one or more images are provided for CAD processing at step 10. A CAD analysis is performed on these image(s) at step 11, and a hash signature is calculated for each image processed by the CAD system at step 12. At step 13, the CAD results are stored, including hash signatures and locators, such as file names or URLs, for the input images. A display system retrieves these CAD results at step 15, and uses the image URLs included with the CAD result data to retrieve the input images and the hash signatures. The display system recalculates the hash signatures on the retrieved images at step 16, and the recalculated hash signature is compared with the retrieved hash signature at step 17. If the two hash signatures are different, the display system knows that something is wrong and takes an appropriate action at step 18, such as presenting an error message to the user, requesting assistance from the user, requesting that the CAD analysis be repeated, etc. Otherwise, if the hash signatures agree, the input image can be displayed with the CAD results at step 19.

According to another embodiment of the invention, the images used by the CAD system can be stored as part of the results, however, this would lead to practical difficulties due to the storage space needed, as well as implementation issues in a large distributed multi-vendor environment. In addition, it would be necessary to ensure that the data stays together or the link between the data remains valid.

In another embodiment of the invention, the image used for CAD analysis is not the same as the image used for display. In this case additional hash signatures should be incorporated to maintain the correspondence between the input image to the CAD algorithm and the image and result data displayed to the user.

According to another embodiment of the invention, the data used for calculating hashes/signatures could include other information, such as the patient name, etc. This information would be helpful, and would help prevent changes to the patient name, while maintaining the usability of the CAD results.

According to another embodiment of the invention, the hashes/signatures could be used as keys by the display system to retrieve the results of the CAD system directly instead of using them only as an extra check, although this would probably require changes to existing storage solutions.

An embodiment of the invention can be applied image processing in general, such as noise removal, etc., wherever CAD is mentioned above. Embodiments of the invention can be applied to other patient related data in addition to images, such as ECGs, etc.

It is to be understood that various modifications to the preferred embodiment and the generic principles and features described herein will be readily apparent to those skilled in the art. Thus, the present invention is not intended to be limited to the embodiment shown but is to be accorded the widest scope consistent with the principles and features described herein.

Furthermore, it is to be understood that the present invention can be implemented in various forms of hardware, software, firmware, special purpose processes, or a combination thereof. In one embodiment, the present invention can be implemented in software as an application program tangibly embodied on a computer readable program storage device. The application program can be uploaded to, and executed by, a machine comprising any suitable architecture.

Figure 2:
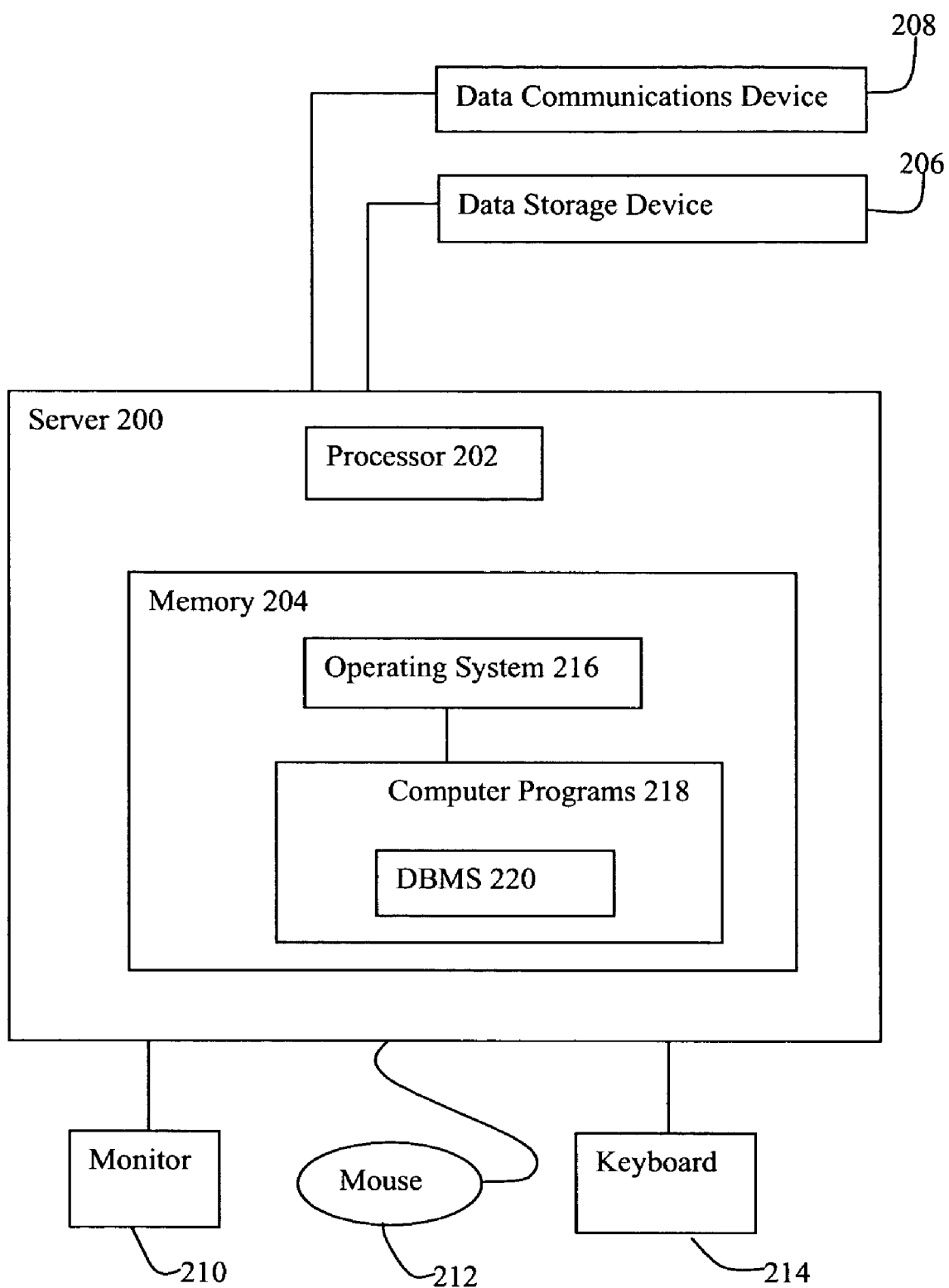
FIG. 2 is a block diagram of an exemplary computer system for implementing a quality assurance method according to an embodiment of the invention.

Accordingly, FIG. 2 illustrates a hardware environment used to implement the present invention. As illustrated in FIG. 2, in the preferred embodiment the present invention is implemented in a server computer ("server") 200. The server 200 generally includes, a processor 202, a memory 204 such as a random access memory (RAM), a data storage device 206 (e.g., hard drive, floppy disk drive, CD-ROM disk drive, etc.), a data communication device 208 (e.g., modem, network interface device, etc.), a monitor (e.g., CRT, LCD display, etc.), a pointing device (e.g., a mouse, a track ball, a pad or any other device responsive to touch, etc.) and a keyboard. It is envisioned that attached to the computer 200 may be other devices such as read only memory (ROM), a video card drive, printers, a signal source, and other peripheral devices including local and wide area network interface devices, etc. One of ordinary skill in the art will recognize that any combination of the above system components may be used to configure the server 200.

The server 200 operates under the control of an operating system ("OS") 216, such as Linux, WINDOWS XP™, WINDOWS NT™, etc., which typically, is loaded into the memory 204 during the server 200 start-up (boot-up) sequence after power-on or reset. In operation, the OS 216 controls the execution by the server 200 of computer programs 218, including server and/or client-server programs. Alternatively, a system and method in accordance with the present invention may be implemented with any one or all of the computer programs 218 embedded in the OS 216 itself to process the signal from the signal source without departing from the scope of an embodiment of the invention. Preferably, however, the client programs are separate from the server programs and may not be resident on the server.

The OS 216 and the computer programs 218 each comprise computer readable instructions which, in general, are tangibly embodied in or are readable from a media such as the memory 204, the data storage device 206 and/or the data communications device 208. When executed by the server 200, the instructions cause the server 200 to perform the steps necessary to implement the present invention. Thus, the present invention may be implemented as a method, apparatus, or an article of manufacture (a computer-readable media or device) using programming and/or engineering techniques to produce software, hardware, firmware, or any combination thereof.

The server 200 is typically used as a part of an information search and retrieval system capable of receiving, retrieving and/or dissemination information over the Internet, or any other network environment. One of ordinary skill in the art will recognize that this system may include more than one of server 200.

In the information search and retrieval system, such as a digital library system, a client program communicates with the server 200 by, inter alia, issuing to the server search requests and queries. The server 200 then responds by providing the requested information. The digital library system is typically implemented using a database management system software (DBMS) 220. The DBMS 220 receives and responds to search and retrieval requests and termed queries from the client. In one embodiment of the invention, the DBMS 220 is server-resident.

Objects are typically stored in a relational database connected to an object server, and the information about the objects is stored in a relational database connected to a library server, wherein the server program(s) operate in conjunction with the (DBMS) 220 to first store the objects and then to retrieve the objects. One of ordinary skill in the art will recognize that the foregoing is an exemplary configuration of a system which embodies the present invention, and that other system configurations such as an ultrasound machine coupled to a workstation via network to access the data in the ultrasound machine may be used without departing from the scope and spirit of the present invention.

While the present invention has been described in detail with reference to a preferred embodiment, those skilled in the art will appreciate that various modifications and substitutions can be made thereto without departing from the spirit and scope of the invention as set forth in the appended claims.

What is claimed is:

1. A method of associating a computer aided detection/diagnosis result with an image comprising the steps of:
   providing one or more digitized images, each image comprising a plurality of intensities corresponding to a domain of points on an N-dimensional grid;
   performing a computer-aided detection/diagnosis of intensity data of a first image;
   calculating a hash signature of intensity of a second input image;
   storing said computer-aided diagnosis results; and
   storing said hash signature, wherein said hash signature verifies said second image when said second image is displayed with said computer-aided diagnosis result.

2. The method of claim 1, wherein said second image is not used as input to said computer aided diagnosis.

3. The method of claim 1, wherein said second image is provided as input for said computer-aided detection/diagnosis.

4. The method of claim 1, further comprising storing a locator for said input image with said computer-aided diagnosis results.

5. The method of claim 1, further comprising storing the input image along with said computer-aided diagnosis results.

6. The method of claim 1, wherein calculating a hash signature comprises submitting said input image to a hash function calculator system that calculates said hash signature.

7. The method of claim 6, further comprising submitting identifying information for said input image to said hash function calculator system for calculating said hash signature.

8. The method of claim 7, wherein said identifying information includes one or more of an image locator, a patient's name, a patient's birth date, a patient's gender, a date of patent's examination wherein said input image was created, an exam type, and a unique identifier of said input image.

9. The method of claim 1, wherein said computer-aided diagnosis results and said hash signature are stored together in a same file.

10. A method of associating a computer aided detection/diagnosis result with an image comprising the steps of:
    providing results of a computer aided detection/diagnosis of a first digitized medical image;
    providing a hash signature of a second medical image to be displayed with said computer aided detection/diagnosis results;
    providing a digitized input image comprising a plurality of intensities corresponding to a domain of points on an N-dimensional grid
    calculating a hash signature of said input image; and
    comparing the hash signature of said input image with the hash signature read from said computer aided diagnosis results.

11. The method of claim 10 further comprising reading a locator for said input image from said computer aided diagnosis results, and using said locator to locate said input image for calculating said hash signature.

12. The method of claim 10, further comprising, if said hash signatures are equal, displaying said input image with said computer aided diagnosis results.

13. The method of claim 10, further comprising submitting said input image to a hash function calculator system that calculates said hash signature of said input image.

14. The method of claim 10, wherein said second medical image corresponds to said computer aided diagnosis results.

15. A program storage device readable by a computer, tangibly embodying a program of instructions executable by the computer to perform the method steps for associating a computer aided detection/diagnosis result with an image said method comprising the steps of:
    providing one or more digitized images, each image comprising a plurality of intensities corresponding to a domain of points on an N-dimensional grid;
    performing a computer-aided detection/diagnosis of intensity data of a first image;
    calculating a hash signature of intensity of a second input image;
    storing said computer-aided diagnosis results; and
    storing said hash signature, wherein said hash signature verifies said second image when said second image is displayed with said computer-aided diagnosis result.

16. The computer readable program-storage device of claim 15, wherein said second image is not used as input to said computer aided diagnosis.

17. The computer readable program storage device of claim 15, wherein said second image is provided as input for said computer-aided detection/diagnosis.

18. The computer readable program storage device of claim 1, the method further comprising storing a locator for said input image with said computer-aided diagnosis results.

19. The computer readable program storage device of claim 15, the method further comprising storing the input image along with said computer-aided diagnosis results.

20. The computer readable program storage device of claim 15, wherein calculating a hash signature comprises submitting said input image to a hash function calculator system that calculates said hash signature.

21. The computer readable program storage device of claim 20, the method further comprising submitting identifying information for said input image to said hash function calculator system for calculating said hash signature.

22. The computer readable program storage device of claim 21, wherein said identifying information includes one or more of an image locator, a patient's name, a patient's birth date, a patient's gender, a date of patent's examination wherein said input image was created, an exam type, and a unique identifier of said input image.

23. The computer readable program storage device of claim 15, wherein said computer-aided diagnosis results and said hash signature are stored together in a same file.

24. A program storage device readable by a computer, tangibly embodying a program of instructions executable by the computer to perform the method steps for associating a computer aided detection/diagnosis result with an image comprising the steps of:
   providing results of a computer aided detection/diagnosis of a first digitized medical image;
   providing a hash signature of a second medical image to be displayed with said computer aided detection/diagnosis results;
   providing a digitized input image comprising a plurality of intensities corresponding to a domain of points on an N-dimensional grid
   calculating a hash signature of said input image; and
   comparing the hash signature of said input image with the hash signature read from said computer aided diagnosis results.

* * * * *